United States Patent
Yanagihara et al.

(10) Patent No.: US 9,517,557 B2
(45) Date of Patent: Dec. 13, 2016

(54) MANIPULATOR

(71) Applicant: OLYMPUS CORPORATION, Tokyo (JP)

(72) Inventors: Masaru Yanagihara, Hachioji (JP); Shingo Nakayama, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 14/827,757

(22) Filed: Aug. 17, 2015

(65) Prior Publication Data

US 2015/0352715 A1 Dec. 10, 2015

Related U.S. Application Data

(63) Continuation of application No. PCT/JP2014/055203, filed on Feb. 25, 2014.

(Continued)

(51) Int. Cl.
*F16H 3/06* (2006.01)
*B25J 9/10* (2006.01)
*B25J 9/06* (2006.01)

(52) U.S. Cl.
CPC ............ *B25J 9/104* (2013.01); *A61B 34/30* (2016.02); *B25J 9/06* (2013.01); *A61B 2034/301* (2016.02);

(Continued)

(58) Field of Classification Search
CPC ........ B25J 9/104; B25J 9/06; Y10T 74/18576; Y10T 74/20323

(Continued)

(56) References Cited

U.S. PATENT DOCUMENTS 5,647,554 A * 7/1997 Ikegami ............... B25J 19/0025
191/12.2 A
5,876,325 A 3/1999 Mizuno et al.
(Continued)

FOREIGN PATENT DOCUMENTS

EP 1721568 A1 11/2006
EP 1787572 A1 5/2007
(Continued)

OTHER PUBLICATIONS

International Search Report and Written Opinion dated Jun. 10, 2014 issued in PCT/JP2014/055203.
(Continued)

*Primary Examiner* — William Kelleher
*Assistant Examiner* — Zakaria Elahmadi
(74) *Attorney, Agent, or Firm* — Scully, Scott, Murphy & Presser, P.C.

(57) ABSTRACT

A manipulator includes an elongated main portion, a distal end portion, and a bendable portion provided between the main portion and the distal end portion; a plurality of linear members that extend from the distal end portion to the main portion via the bendable portion; a power generator; a plurality of power transmitters that transmit, to proximal ends of the linear members, the power generated by the power generator as linear motion in a longitudinal direction of the main portion; and a linear-member relaxing unit that relaxes the linear members in which tension is generated between the distal end portion and the power transmitters by pushing and pulling of the linear members by the linear motion transmitted from the power transmitters.

10 Claims, 19 Drawing Sheets

Related U.S. Application Data

(60) Provisional application No. 61/770,556, filed on Feb. 28, 2013, provisional application No. 61/769,979, filed on Feb. 27, 2013.

(52) U.S. Cl.
CPC ......... *A61B 2034/306* (2016.02); *Y10S 901/15* (2013.01); *Y10S 901/21* (2013.01); *Y10T 74/18576* (2015.01); *Y10T 74/20323* (2015.01)

(58) Field of Classification Search
USPC ...................... 74/89.23; 606/1, 130, 139, 202
See application file for complete search history.

(56) References Cited

U.S. PATENT DOCUMENTS

| | | | | |
|---|---|---|---|---|
| 7,331,436 | B1* | 2/2008 | Pack | B65H 75/425 |
| | | | | 191/12.2 A |
| 7,699,835 | B2* | 4/2010 | Lee | A61B 17/062 |
| | | | | 606/1 |
| 2003/0135204 | A1* | 7/2003 | Lee | A61B 90/36 |
| | | | | 606/1 |
| 2005/0107667 | A1* | 5/2005 | Danitz | A61B 1/0053 |
| | | | | 600/139 |
| 2006/0287576 | A1 | 12/2006 | Tsuji et al. | |
| 2007/0150155 | A1 | 6/2007 | Kawai et al. | |
| 2008/0119695 | A1 | 5/2008 | Ueno et al. | |
| 2009/0112230 | A1* | 4/2009 | Jinno | B25J 9/104 |
| | | | | 606/130 |
| 2011/0065994 | A1 | 3/2011 | Kudoh et al. | |
| 2012/0004648 | A1 | 1/2012 | Choi et al. | |
| 2012/0065628 | A1* | 3/2012 | Naito | A61B 1/00078 |
| | | | | 606/1 |
| 2012/0209253 | A1* | 8/2012 | Donhowe | A61B 17/00 |
| | | | | 606/1 |
| 2013/0165908 | A1* | 6/2013 | Purdy | A61F 5/0013 |
| | | | | 606/1 |
| 2014/0094825 | A1* | 4/2014 | Flaherty | A61B 19/2203 |
| | | | | 606/130 |

FOREIGN PATENT DOCUMENTS

| | | |
|---|---|---|
| EP | 1902665 A1 | 3/2008 |
| EP | 2229868 A1 | 9/2010 |
| EP | 2305144 A1 | 4/2011 |
| JP | H05-049594 A | 3/1993 |
| JP | H05-329097 A | 12/1993 |
| JP | H06-269398 A | 9/1994 |
| JP | H07-013453 A | 1/1995 |
| JP | H07-134253 A | 5/1995 |
| JP | H07-171093 A | 7/1995 |
| JP | H08-164141 A | 6/1996 |
| JP | 2001-095754 A | 4/2001 |
| JP | 2003-019683 A | 1/2003 |
| JP | 2005-279253 A | 10/2005 |
| JP | 2006-055349 A | 3/2006 |
| JP | 2006-061176 A | 3/2006 |
| JP | 2006061176 A * | 3/2006 |
| JP | 2006-141624 A | 6/2006 |
| JP | 2007-020797 A | 2/2007 |
| JP | 2009-225992 A | 10/2009 |
| JP | 2010-213969 A | 9/2010 |
| WO | WO 2010/109932 A1 | 9/2010 |

OTHER PUBLICATIONS

Partial Supplementary European Search Report dated Sep. 21, 2016 in related European Application No. 14 75 7515.3.

* cited by examiner

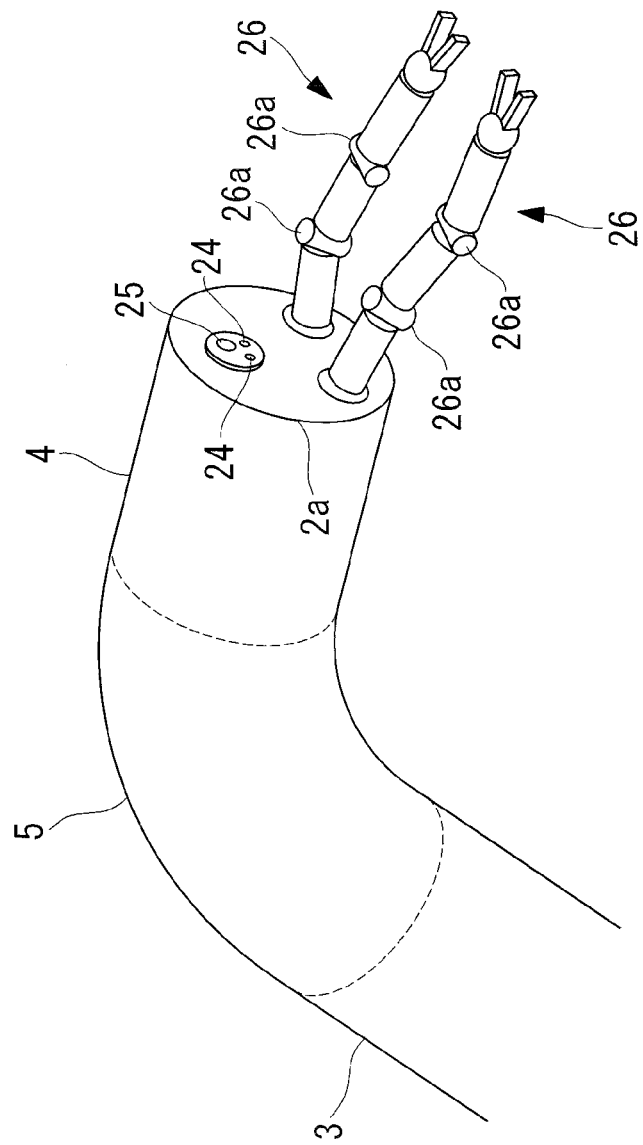

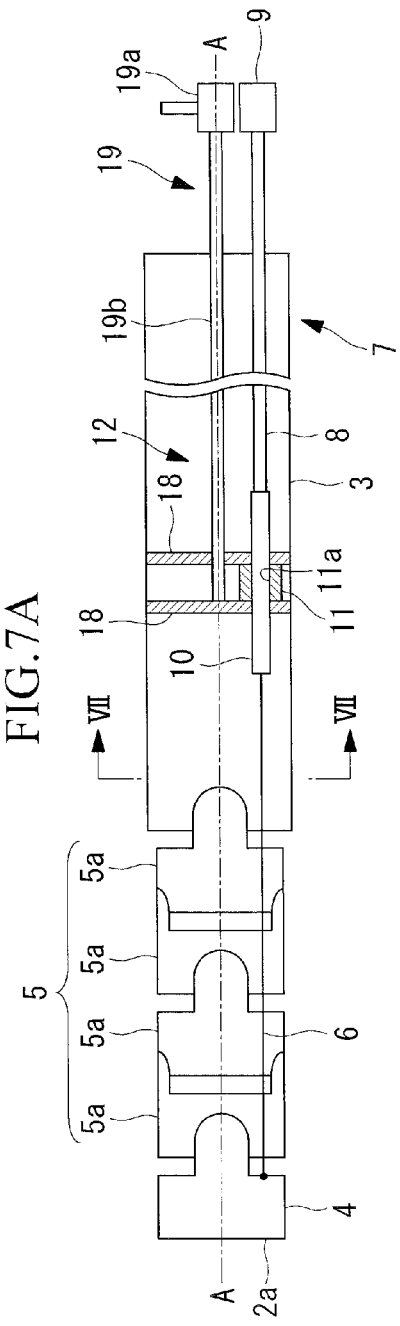
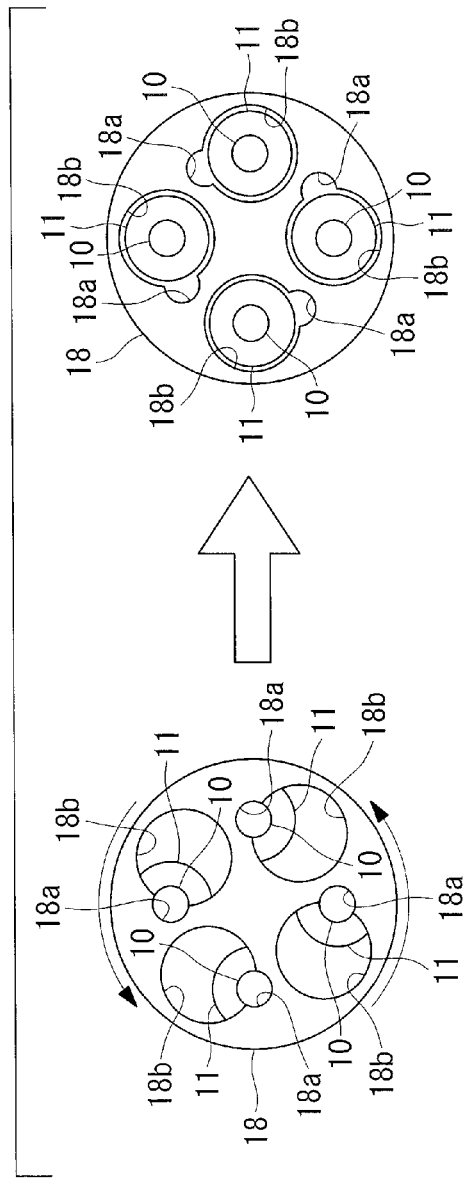
FIG.7A
FIG.7B

MANIPULATOR

CROSS-REFERENCE TO RELATED APPLICATIONS

This is a continuation of International Application PCT/JP2014/055203, with an international filing date of Feb. 25, 2014, which is hereby incorporated by reference herein in its entirety. This application claims the benefits of U.S. Provisional Patent Application No. 61/769,979, filed on Feb. 27, 2013, and No. 61/770,556, filed on Feb. 28, 2013, the contents of which are incorporated herein by reference.

TECHNICAL FIELD

The present invention relates to manipulators.

BACKGROUND ART

In the related art, there is a known medical manipulator that is equipped with an elongated insertion section insertable into a body and that is used for treating the inside of the body by remotely manipulating a surgical tool installed in the insertion section (for example, see Patent Literature 1). The insertion section of such a manipulator is provided with a bendable portion for changing the orientation of a distal end surface equipped with, for example, a camera and the surgical tool.

Furthermore, in order to accurately control the bending angle of the bendable portion, a decelerating mechanism is used in a bending mechanism for bending the bendable portion. Specifically, with this configuration, large rotational motion of a shaft generated at the proximal end of the insertion section is converted into small linear motion by a threaded shaft that rotates together with the shaft and by a nut engaged with the threaded shaft. By utilizing this linear motion, wires connected to the distal end of the insertion section are pushed and pulled, thereby bending the bendable portion.

CITATION LIST

Patent Literature

{PTL 1}
Japanese Unexamined Patent Application, Publication No. 2006-61176

SUMMARY OF INVENTION

A first aspect of the present invention is a manipulator including an elongated main portion, a distal end portion disposed at a distal end of the main portion, and a bendable portion provided between the main portion and the distal end portion; a plurality of linear members that are connected to the distal end portion and that extend to the main portion via the bendable portion; a power generator that generates power; a plurality of power transmitters that are provided in the main portion and that transmit, to proximal ends of the linear members, the power generated by the power generator as linear motion in a longitudinal direction of the main portion; and a linear-member relaxing unit that relaxes the plurality of linear members in which tension is generated between the distal end portion and the power transmitters by being pushing and pulling of the linear members in the longitudinal direction by the linear motion transmitted from the power transmitters.

A second aspect of the present invention is a manipulator including an elongated main portion, a distal end portion disposed at a distal end of the main portion, and a bendable portion provided between the main portion and the distal end portion; a plurality of linear members that are connected to the distal end portion and that extend to the main portion via the bendable portion; a plurality of pulling mechanisms provided in the main portion and having connectors that are connected to proximal ends of the linear members, drivers that generate rotational motion, and power converters that convert the rotational motion generated by the drivers into linear motion in a longitudinal direction and transmit the linear motion to the connectors; and a combination changing mechanism that changes a combination of the linear members and the pulling mechanisms connected to the linear members.

BRIEF DESCRIPTION OF DRAWINGS

FIG. 2 is a perspective view illustrating the configuration of a part of a distal end of a manipulator included in the surgical manipulator system in FIG. 1.

FIG. 7A illustrates another modification of the linear-member relaxing unit.

FIG. 7B is a diagram explaining the operation of the linear-member relaxing unit in FIG. 7A.

DESCRIPTION OF EMBODIMENTS

First Embodiment

A manipulator 1 and a surgical manipulator system 100 equipped with the same according to a first embodiment of the present invention will be described below with reference to the drawings.

Figure 1:
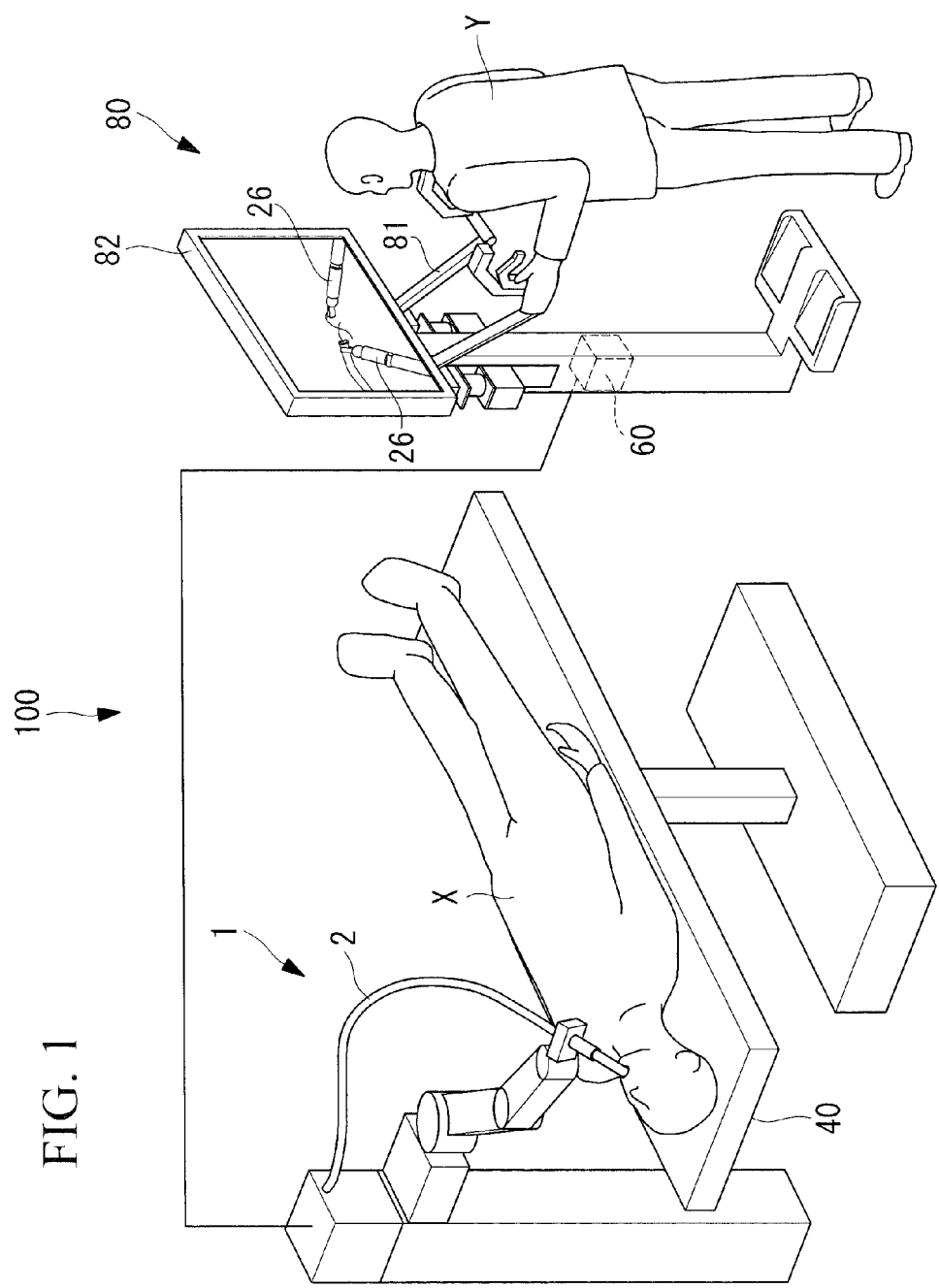
FIG. 1 illustrates the overall configuration of a surgical manipulator system according to a first embodiment of the present invention.

FIG. 1 schematically illustrates the surgical manipulator system 100 according to this embodiment. As shown in FIG. 1, the surgical manipulator system 100 includes the manipulator 1 disposed in the vicinity of a bed 40 on which a patient X lies down, a control device 60 connected to the manipulator 1, and a manipulation device 80 used for inputting a manipulation signal for the manipulator 1 to the control device 60.

FIG. 2 illustrates a part of a distal end of the manipulator 1 according to this embodiment. As shown in FIG. 2, a distal end surface 2a of the manipulator 1 is provided with a light unit 24 that emits illumination light and a camera 25 that acquires an image of the inside of a body, and the manipulator 1 is provided with a surgical tool 26 that is protrudable and retractable from the distal end surface 2a. The surgical tool 26 protruding from the distal end surface 2a is disposed within the field of view of the camera 25. As will be described later, the orientation of the distal end surface 2a of the manipulator 1 can be changed by bending a bendable portion 5 thereof, so that the image acquisition range of a treatment site of the patient X can be arbitrarily changed.

The manipulation device 80 includes an input unit 81, such as a joystick, manipulated by a surgeon Y and a display unit 82 that displays the image acquired by the camera 25.

In accordance with an input from the input unit 81, the control device 60 outputs a command signal to each section of the manipulator 1. Based on these command signals, the protruding-retracting operation of the surgical tool 26, the rotating operation of joints 26a thereof, and the bending operation of the bendable portion 5 are controlled. As will be described later, if the manipulator 1 is faulty, the control device 60 is configured to control the entire surgical manipulator system 100 in accordance with a preset program.

The surgeon Y can treat the inside of the body of the patient X by remotely manipulating the surgical tool 26 and the bendable portion 5 of the manipulator 1 via the input unit 81 of the manipulation device 80 while observing, on the display unit 82, the image of the surgical tool 26 and the inside of the body acquired by the camera 25.

Next, the manipulator 1 according to this embodiment will be described in detail.

The manipulator 1 includes, for example, an elongated insertion section 2 that is to be inserted into the body of the patient X from the mouth thereof. The insertion section 2 includes an elongated main portion 3, a distal end portion 4 disposed at the distal end of the main portion 3, and the bendable portion 5 that is disposed between the main portion 3 and the distal end portion 4 and that connects these portions.

The main portion 3 is a flexible portion that is bendable in conformity to the tissue form within the body of the patient X.

The distal end portion 4 is a rigid, sufficiently compact portion where, for example, the light unit 24, the camera 25, and the surgical tool 26 described above are installed.

Figure 3A:
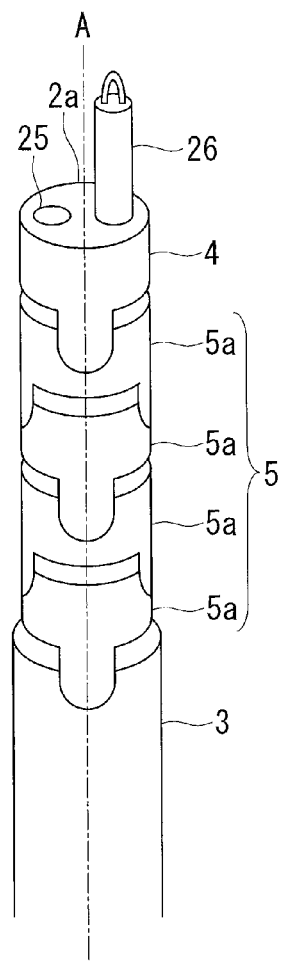
FIG. 3A schematically illustrates a bendable portion in a straightened state.
Figure 3B:
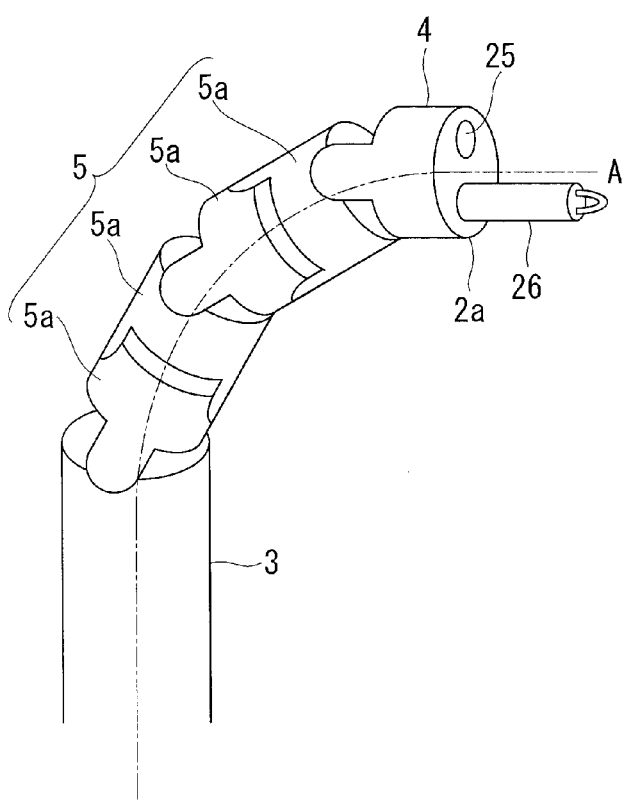
FIG. 3B schematically illustrates the bendable portion in a bent state.

The bendable portion 5 bends in a direction that intersects the longitudinal direction of the main portion 3 so as to orient the distal end surface 2a in an arbitrary direction, as described above. As shown in FIG. 3A, the bendable portion 5 includes a plurality of cylindrical joint rings 5a that are arranged along a central axis (sometimes simply referred to as "axis" hereinafter) A of the insertion section 2. The joint rings 5a are connected to the another adjoining joint rings 5a in a swingable manner about two axes that are orthogonal to the axis A. Thus, the bendable portion 5 is bendable in an arbitrary direction, as shown in FIG. 3B. The configuration of the bendable portion 5 is not limited to the structure that uses the joint rings 5a (i.e., bendable pieces), and may alternatively be, for example, a flexural mechanism based on a multi-joint structure.

Referring to FIG. 4, as a bending mechanism that controls the bending operation of the bendable portion 5, the manipulator 1 includes wires (linear members) 6 whose distal ends are connected to the distal end portion 4 and that extend in the direction of the axis A to the main portion 3, and pulling mechanisms 7 that are provided in the main portion 3 and that pull the wires 6. The pulling mechanisms 7 each include a flexible shaft 8 disposed along the axis A, a motor (power generator) 9 provided at the proximal end of the shaft 8, a threaded shaft (threaded shaft member) 10 that is coaxial with the shaft 8 and connects the shaft 8 and the proximal end of the corresponding wire 6, and a nut (nut member) 11 with which the threaded shaft 10 is engaged. The shaft 8 is expandable and contractible or has a sufficient length so that the threaded shaft 10 can advance and retract in the direction of the axis A.

Each of the wires 6 may be composed of a rigid material that can transmit motion at the proximal end thereof to the distal end thereof. For example, metal or plastic is preferred. Although the wires 6 are used as linear members in this embodiment, the linear members are not limited to this form and may alternatively be, for example, rods, tubes, or metal coils.

Each motor 9 generates a rotational force that causes the corresponding shaft 8 to rotate about a central axis extending in the longitudinal direction thereof. When the shaft 8 rotates in the forward or reverse direction, the corresponding threaded shaft 10 rotates in the forward or reverse direction together with the shaft 8. The nut 11 has four female screws 11a with which the four threaded shafts 10 are engaged, respectively, and simultaneously supports the four threaded shafts 10. Moreover, the nut 11 is fitted within the main portion 3 and is positionally set in the direction of the axis A relative to the main portion 3 by the operation of a moving mechanism 13 to be described later. The nut 11 transmits the rotating threaded shafts 10 toward the distal end or the proximal end of the main portion 3 in the direction of the axis A. When the threaded shafts 10 advance toward the distal end, the wires 6 pushed toward the distal end press the distal end portion 4 toward the distal end. When the threaded shafts 10 retract toward the proximal end, the wires 6 pulled toward the proximal end pull the distal end portion 4 toward the proximal end. Although this causes the shafts 8 to expand or contract or to become slack, the effect this may have on the bendable portion 5 is negligible since the motors 9 and the nut 11 joined to the ends of the shafts 8 are fixed to or positioned relative to the main portion 3.

Figure 4A:
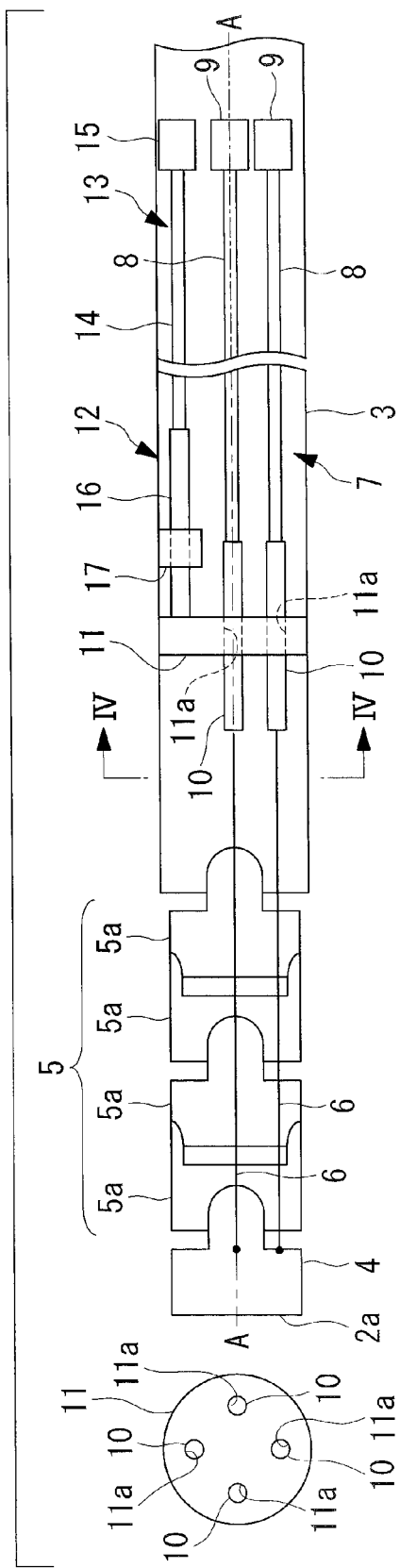
FIG. 4A illustrates the configuration of a bending mechanism included in the manipulator.
Figure 4B:
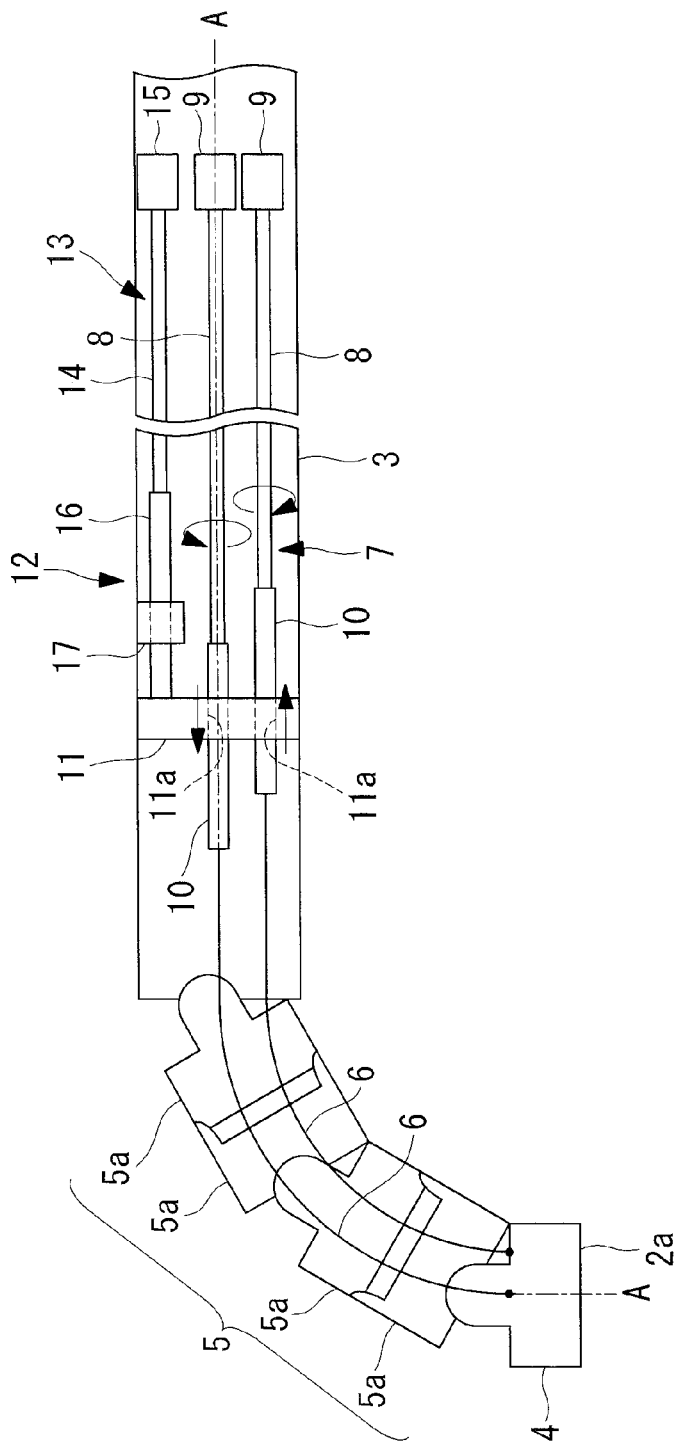
FIG. 4B is a diagram explaining the operation of the bending mechanism in FIG. 4A.

As shown at the left side of FIG. 4A, four sets of wires 6 and pulling mechanisms 7 are provided and are spaced apart from each other around a circumference centered on the axis A. In the other drawings, only one set or two sets of wires 6 and pulling mechanisms 7 is/are illustrated to simplify the drawings. Of the four wires 6, some of them are pushed out, whereas the remaining wires are pulled, causing the bendable portion 5 to bend as shown in FIG. 4B. By adjusting the amounts of pushing and pulling of the wires 6, the bending angle of the bendable portion 5 can be controlled.

Furthermore, the manipulator 1 includes a wire relaxing unit 12 that relaxes the wires 6 in which tension is generated between the distal end portion 4 and the threaded shafts 10 due to actuation of the pulling mechanisms 7. The wire relaxing unit 12 is formed of the single nut (supporting member) 11 that simultaneously supports the four threaded shafts 10, as described above, and the moving mechanism 13 that moves the nut 11 toward the distal end along the axis A.

The moving mechanism 13 includes a flexible shaft (power converter) 14 disposed along the axis A, a motor (rotational-force generator) 15 provided at the proximal end of the shaft 14, a threaded shaft (power converter) 16 that is coaxial with the shaft 14 and connects the shaft 14 and the nut 11, and a nut (power converter) 17 that is fixed to the main portion 3 and is engaged with the threaded shaft 16. Similar to the pulling mechanisms 7, the moving mechanism 13 rotates the shaft 14 by utilizing a rotational force generated by the motor 15, converts this rotational motion into linear motion in the direction of the axis A by means of the threaded shaft 16 and the nut 17, and transmits the linear motion to the nut 11. Consequently, the nut 11 is moved in the direction of the axis A.

The shaft 14, the motor 15, the threaded shaft 16, and the nut 17 of the moving mechanism 13 are all provided separately from the shaft 8, the motor 9, the threaded shaft 10, and the nut 11 of each pulling mechanism 7, such that the moving mechanism 13 is configured to operate independently of the pulling mechanisms 7.

Next, the operation of the surgical manipulator system 100 equipped with the manipulator 1 having the above-described configuration will be described.

In order to treat a treatment site of the patient X by using the surgical manipulator system 100 according to this embodiment, the surgeon Y first actuates the manipulator 1 by manipulating the input unit 81 and adjusts the position and the orientation of the distal end surface 2a by changing the bending direction and the bending angle of the bendable portion 5 so that the treatment site is set within the field of view of the camera 25.

Subsequently, the surgeon Y manipulates the input unit 81 to cause the surgical tool 26 to protrude from the distal end surface 2a so that the surgical tool 26 is moved to the field of view of the camera 25. The surgeon Y can treat the treatment site by remotely manipulating the surgical tool 26 via the input unit 81 while observing the positional relationship between the treatment site and the surgical tool 26 in the image displayed on the display unit 82.

Figure 5A:
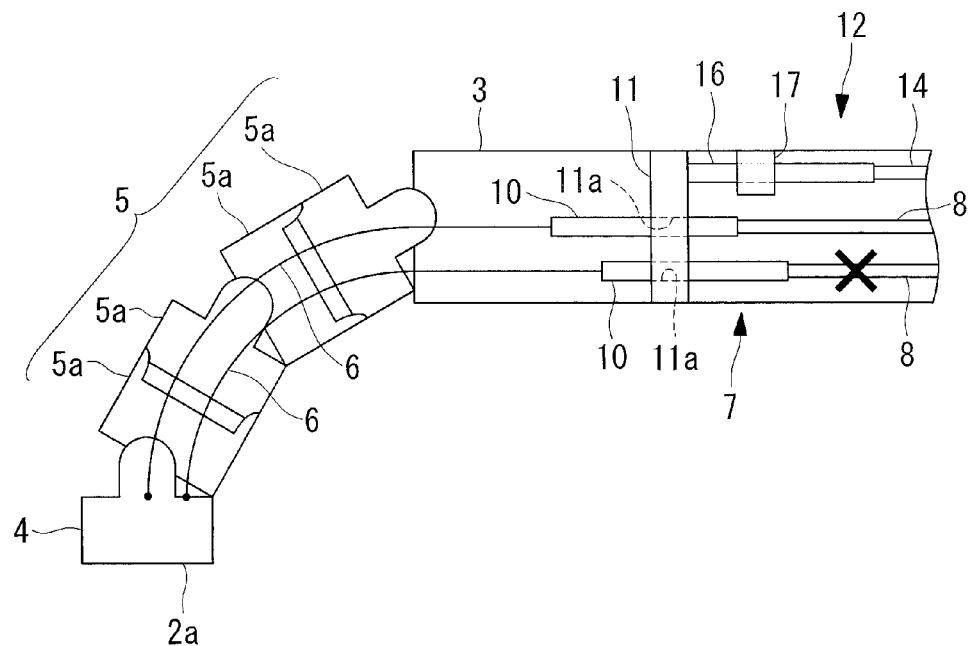
FIG. 5A is a diagram explaining the operation of a linear-member relaxing unit included in the manipulator.

Referring to FIG. 5A, if, for example, the shaft 8 of any of the pulling mechanisms 7 breaks during the manipulation of the manipulator 1 and the power from the corresponding motor 9 is not transmitted to the proximal end of the corresponding wire 6, the bending angle of the bendable portion 5 would not change in response to an input manipulation performed on the input unit 81 by the surgeon Y, and the field of view of the camera 25 displayed on the display unit 82 would not move properly. Therefore, the surgeon Y can readily recognize a fault in the pulling mechanism 7.

In the configuration that drives the wires 6 by converting relatively large rotational motion generated by the motors 9 into relatively small linear motion via the threaded shafts 10 and the nut 11, the wires 6 need to be linearly moved by a sufficiently large force in order to rotate the threaded shafts 10 and the shafts 8 with the linear motion of the wires 6. Specifically, even if a pressing force were applied to the distal end portion 4 and the bendable portion 5 from the tissues within the body, this pressing force is not enough to move the wires 6 in the direction of the axis A and deform the bendable portion 5, thus causing the bendable portion 5 to continue to maintain a certain shape against the tissue form within the body.

Figure 5B:
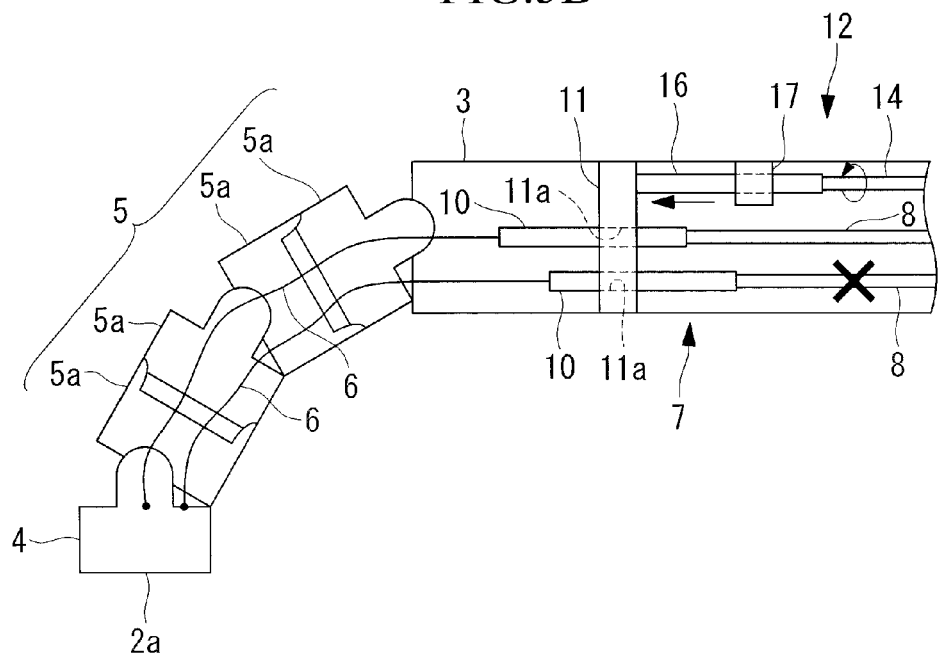
FIG. 5B is a diagram explaining the operation of the linear-member relaxing unit included in the manipulator.

Thus, the surgeon Y actuates the wire relaxing unit 12 after determining that a pulling mechanism 7 is faulty. Specifically, as shown in FIG. 5B, by actuating the motor 15, the threaded shaft 16 is moved toward the distal end, causing the nut 11 to move toward the distal end. With the movement of the nut 11 toward the distal end, the distance between the distal end portion 4 and each threaded shaft 10 becomes shorter than the length of the corresponding wire 6, whereby all of the wires 6 become sufficiently relaxed at the same time. In this state, the bendable portion 5 can be flexibly deformed in accordance with the pressing force from the tissues within the body. Therefore, the surgeon Y can smoothly move and pull out the insertion section 2 along the tissue form within the body.

Accordingly, with this embodiment, when a pulling mechanism 7 becomes faulty, the four wires 6 are simultaneously relaxed by the wire relaxing unit 12 that operates independently of the pulling mechanisms 7, whereby the bendable portion 5 can be set in a flexible state. This is advantageous in that the surgeon Y can smoothly remove the manipulator 1 from the body.

As an alternative to or in addition to the configuration of this embodiment in which the wire relaxing unit 12 reduces the distance between the distal end portion 4 and the threaded shafts 10 by moving the nut 11 toward the distal end, the distal end portion 4 may be moved toward the proximal end.

Figure 6:
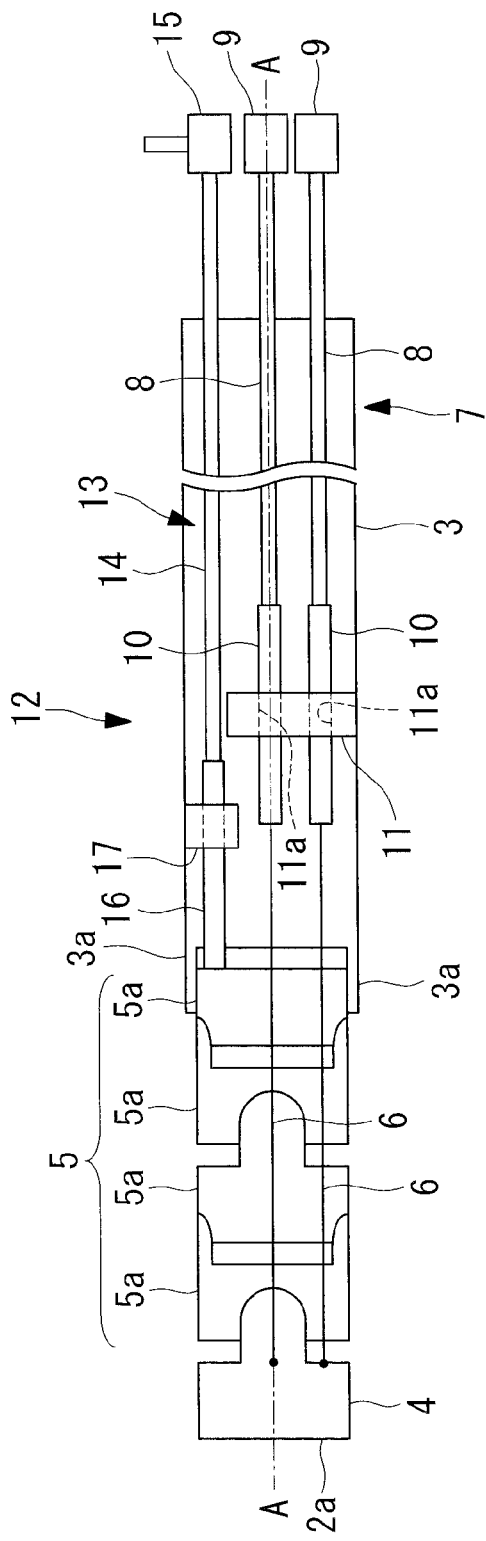
FIG. 6 illustrates a modification of the linear-member relaxing unit.

Referring to FIG. 6, in this modification, the distal end of the threaded shaft 16 is connected to the joint ring 5a disposed at the most proximal side of the bendable portion 5. The threaded shaft 16 and the joint ring 5a at the most proximal side are connected via a ball-shaped joint (not shown) such that the rotation of the threaded shaft 16 is not transmitted to this joint ring 5a. Moreover, the outer periphery of this joint ring 5a is slidable along the inner periphery of a guide 3a of the main portion 3, and this joint ring 5a is positionally set in the direction of the axis A by the threaded shaft 16.

Accordingly, the shaft 14 and the threaded shaft 16 are rotated by actuating the motor 15 of the wire relaxing unit 12. When the threaded shaft 16 moves toward the proximal end, the bendable portion 5 is pulled toward the proximal end, and the distal end portion 4 connected to the bendable portion 5 is also pulled toward the proximal end. The distance between the distal end portion 4 and the threaded shafts 10 can also be reduced in this manner.

Furthermore, in this embodiment, instead of the wire relaxing unit 12 driving the nut 11 in the direction of the axis A, the distance between the distal end portion 4 and the threaded shafts 10 may be changed by allowing the wire relaxing unit 12 to set the nut 11 in a movable manner in the direction of the axis A after positioning the nut 11 in the direction of the axis A.

Referring to FIG. 7A, in this modification, the wire relaxing unit 12 includes a positioning member 18 that sets nuts 11 at predetermined positions in the direction of the axis A, and a positioning releasing mechanism 19 that releases each nut 11 positioned by the positioning member 18.

The positioning member 18 is formed of two plate components (also referred to as "plate components 18" hereinafter) that sandwich the nuts 11 in the direction of the axis A. As shown in FIG. 7B, the two plate components 18 each have cutouts 18a each having a diameter smaller than the diameter of each nut 11 and into which the corresponding threaded shaft 10 fits, and large-diameter holes 18b each communicating with the corresponding cutout 18a in a circumferential direction centered on the axis A and having a diameter larger than the diameter of each nut 11. Moreover, the peripheral edges of the two plate components 18 are fitted into, for example, grooves formed circumferentially around the inner peripheral surface of a tube serving as an outer sheath for the main portion 3, so that the plate components 18 are rotatable about the axis A while being fixed in position in the direction of the axis A. As shown at the left side of FIG. 7B, the two plate components 18 lock the movement of the nuts 11 in the direction of the axis A in a state where the threaded shafts 10 are fitted in the cutouts 18a, whereby the positioning member 18 positions the nuts 11 in the direction of the axis A.

The positioning releasing mechanism 19 includes a manipulable section 19a that is rotated by the surgeon Y at the proximal end of the main portion 3, and a shaft 19b that is disposed in alignment with the axis A, connects the two plate components 18 to the manipulable section 19a, and transmits rotational motion about the axis A generated via the manipulable section 19a to the two plate components 18. The shaft 19b has super-elasticity corresponding to the flexibility of the main portion 3. When the surgeon Y rotates the manipulable section 19a, the two plate components 18 rotate about the axis A, causing the threaded shafts 10 fitted in the cutouts 18a to move to the large-diameter holes 18b, as shown at the right side of FIG. 7B. In the large-diameter holes 18b, the threaded shafts 10 and the nuts 11 become movable in the direction of the axis A.

Therefore, after rotating the manipulable section 19a, the surgeon Y may push the shafts 8 of the pulling mechanisms 7 toward the distal end from the proximal end of the main portion 3 so as to reduce the distance between the distal end portion 4 and the threaded shafts 10, thereby simultaneously relaxing the four wires 6.

In this embodiment, the wire relaxing unit 12 is configured to convert rotational motion generated by the motor 15 into linear motion and transmit the linear motion to the nut 11. Alternatively, linear motion in the direction of the axis A may be generated at the proximal end of the main portion 3, and the linear motion may be directly transmitted to the nut 11.

Figure 8:
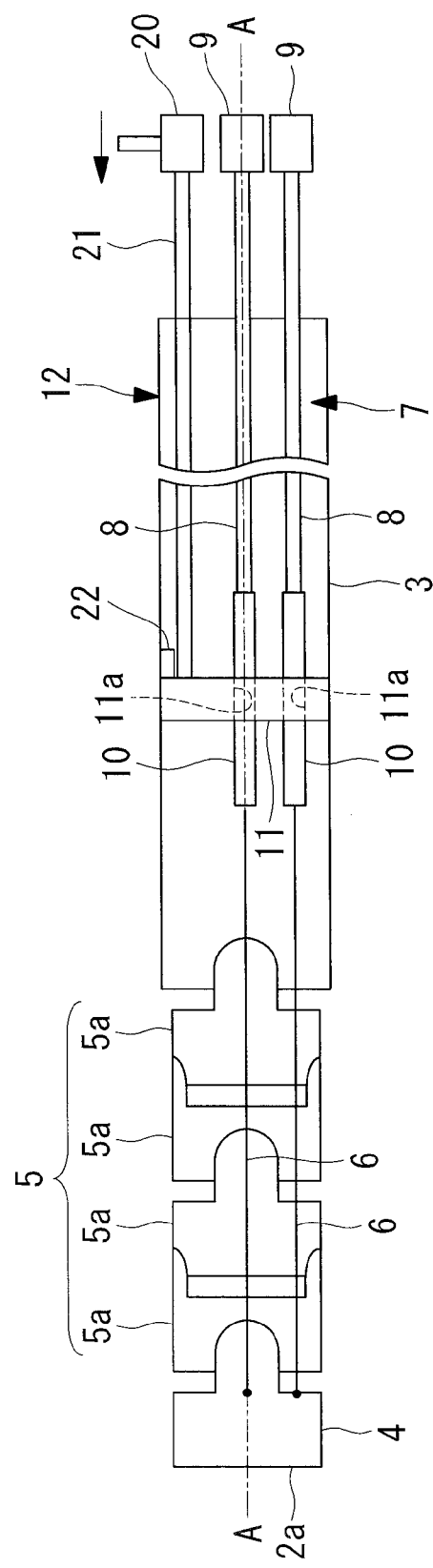
FIG. 8 illustrates another modification of the linear-member relaxing unit.

Referring to FIG. 8, in this modification, the wire relaxing unit 12 includes a manipulable section 20 that is moved in the direction of the axis A by the surgeon Y from the proximal end of the main portion 3, and a flexible shaft 21 that connects the manipulable section 20 to the nut 11 and transmits linear motion of the manipulable section 20 to the nut 11. Reference numeral 22 denotes a stopper that prevents the nut 11 from moving toward the proximal end.

Accordingly, with a simple manipulation performed by the surgeon Y for pushing the manipulable section 20 toward the distal end, the distance between the distal end portion 4 and the threaded shafts 10 is reduced, whereby the four wires 6 can be simultaneously relaxed.

In this embodiment, the surgeon Y actuates the wire relaxing unit 12 manually when the surgeon Y determines that a pulling mechanism 7 is faulty. Alternatively, referring to FIG. 9, the manipulator 1 may include a fault detector 23 that detects a fault in a pulling mechanism 7.

The fault detector 23 includes, for example, a curvature sensor 231 that detects the bending angle of the bendable portion 5 and a fault determination circuit 232 that compares the bending angle detected by the curvature sensor 231 with a bending angle defined by a command signal transmitted from the control device 60 to each motor 9.

The curvature sensor 231 transmits the detected bending angle of the bendable portion 5 to the fault determination circuit 232. The fault determination circuit 232 receives the command signal output from the control device 60 to the motor 9. If a difference between the bending angle from the curvature sensor 231 and the bending angle defined by the command signal is larger than a predetermined threshold value, the fault determination circuit 232 determines that the pulling mechanism 7 to which the motor 9 belongs is faulty, and transmits the determination result to the control device 60.

The curvature sensor 231 is, for example, an optical fiber that is disposed along the axis A in the bendable portion 5 and that is bendable together with the bendable portion 5. The optical fiber is provided with notches in the outer peripheral surface thereof at a plurality of locations in the longitudinal direction such that, when the optical fiber is in a bent state, light leaks from the notches. The amount of light leakage is correlated with the bending angle of the optical fiber. Therefore, the bending angle of the bendable portion 5 can be detected on the basis of the amount of light leakage from the optical fiber.

In place of the optical fiber, a wire sensor or an image sensor may be used.

A wire sensor includes a detection wire disposed substantially parallel to the wires 6 of the bending mechanism and detects the bending angle of the bendable portion 5 on the basis of an amount of movement of the detection wire in the direction of the axis A, which occurs due to the bending of the bendable portion 5.

An image sensor uses the camera 25 to acquire an image of a predetermined marker given to the surgical tool 26 and analyzes the acquired image to detect the bending angle of the bendable portion 5 on the basis of the photographed angle of the marker.

As another alternative, the fault detector 23 may detect a fault in a pulling mechanism 7 by using an electric-current sensor or a distortion sensor in place of the curvature sensor 231.

An electric-current sensor detects an electric current flowing through each motor 9. If the electric-current sensor detects an electric current that is excessively high or low relative to the electric current that can flow through the motor 9 in the normal state, the fault determination circuit 232 determines that the corresponding pulling mechanism 7 is faulty.

A distortion sensor measures stress generated in each shaft 8. If the distortion sensor detects stress that is excessively high or low relative to the stress generated in the shaft 8 in the normal state, the fault determination circuit 232 determines that the corresponding pulling mechanism 7 is faulty.

Figure 10:
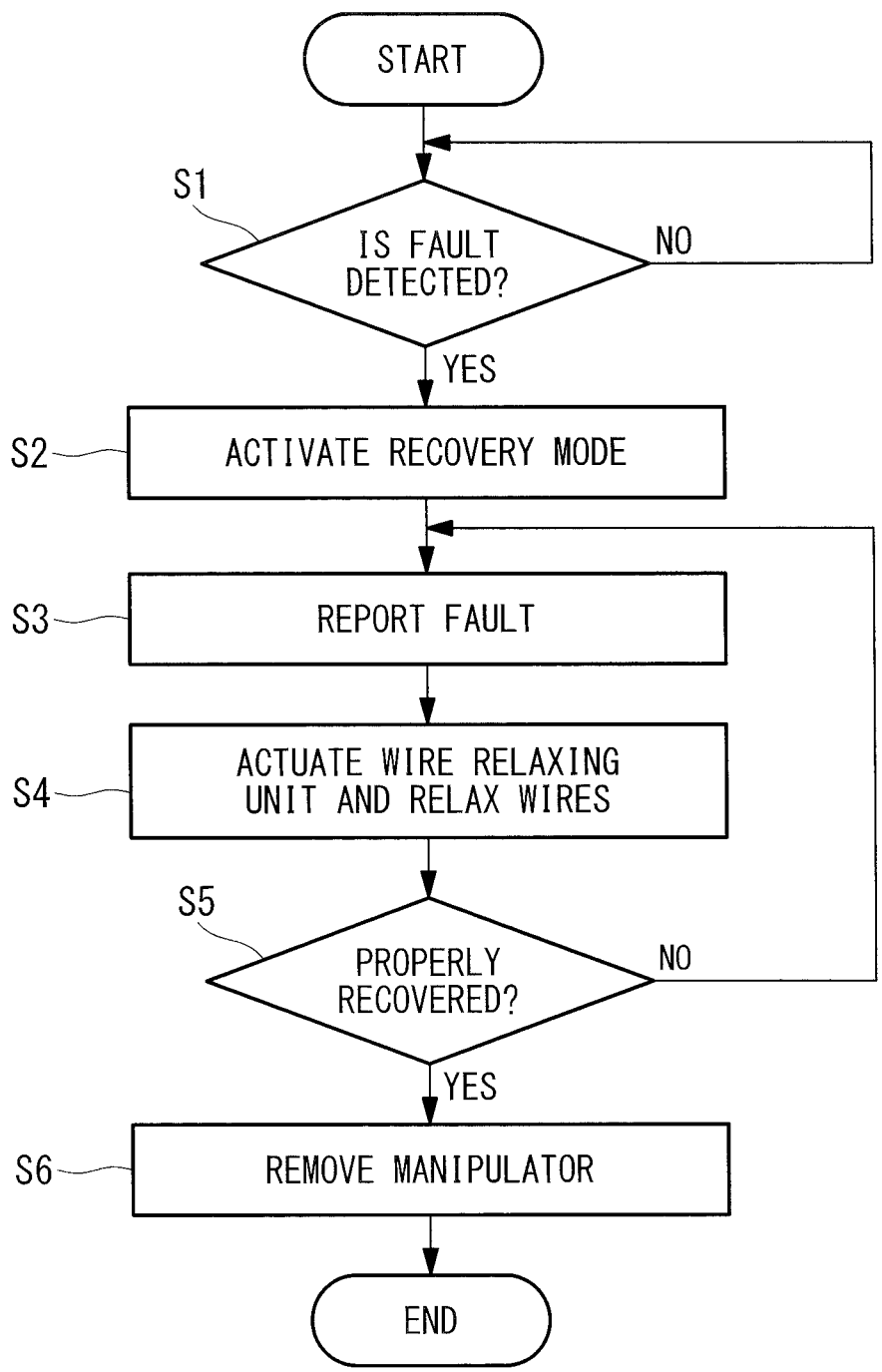
FIG. 10 is a flowchart explaining the operation of the surgical manipulator system equipped with the fault detector in FIG. 9 when a pulling mechanism is faulty.

In the case where a fault in a pulling mechanism 7 is to be detected automatically by the fault detector 23 in this manner, the control device 60 may execute a process for relaxing the wires 6 in accordance with a preset program, as shown in FIG. 10.

Specifically, when the fault detector 23 detects a fault in a pulling mechanism 7 (YES in step S1), the control device 60 activates a recovery mode (step S2). In the recovery mode, the control device 60 first notifies the surgeon Y of the fault (step S3).

The surgeon Y is notified by, for example, displaying a warning message on the display unit 82, turning on a lamp, or setting off a warning alarm. As an alternative to or in addition to such a notification, the control device 60 may add limitations to the manipulation of the manipulator 1 by the surgeon Y, such as prohibiting control of the manipulator 1 by the surgeon Y via the input unit 81 or delaying the movement of the manipulator 1 by exerting a load on the manipulation performed on the input unit 81 by the surgeon Y.

Subsequently, the control device 60 actuates the wire relaxing unit 12 so as to relax the four wires 6 (step S4). In this case, the control device 60 checks whether or not the bending angle of the bendable portion 5 has properly changed in response to the actuation of the wire relaxing unit 12 on the basis of the bending angle detected by the curvature sensor 231 of the fault detector 23 (step S5). Then, the manipulator 1 is removed from the body (step S6).

Accordingly, a fault in a pulling mechanism 7 can be detected more reliably, and the load on the surgeon Y can be reduced. Alternatively, the surgeon Y may detect a fault in a pulling mechanism 7 and manually activate the recovery mode, and the process from step S3 to step S5 may be performed automatically by the control device 60.

Second Embodiment

Next, a manipulator 1 and a surgical manipulator system 100 equipped with the same according to a second embodiment of the present invention will be described below with reference to the drawings. In this embodiment, description of the configuration in common with the first embodiment will be omitted.

In the surgical manipulator system 100 according to this embodiment, as will be described later, if the manipulator 1 is faulty, the control device 60 is configured to control the entire surgical manipulator system 100 in accordance with a preset program.

Figure 11:
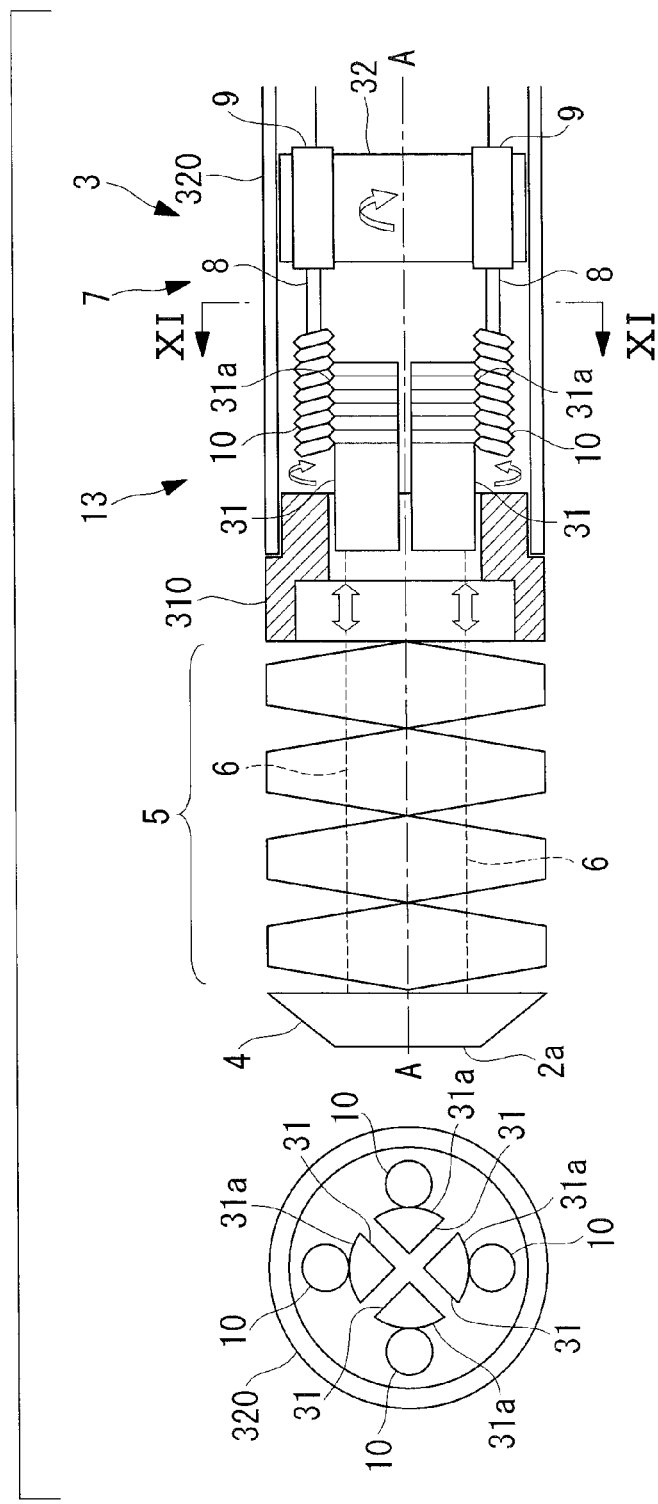
FIG. 11 includes a longitudinal sectional view (right side) illustrating the configuration of a bending mechanism included in the manipulator according to a second embodiment of the present invention and a cross-sectional view (left side) taken along line XI-XI.

In this embodiment, as shown at the left side of FIG. 11, four sets of wires 6 and pulling mechanisms 7 are provided and are spaced apart from each other at substantially equal distances around a circumference centered on the axis A. In other words, the wires 6 and the pulling mechanisms 7 are disposed in a 45°-rotationally-symmetrical arrangement with respect to the axis A.

The pulling mechanisms 7 each include a shaft 8 disposed along the axis A, a motor (driver) 9 provided at the proximal end of the shaft 8, a threaded shaft (threaded shaft member, connector) 10 that is provided at the distal end of the shaft 8 and that is coaxial with the shaft 8, and a movable member (connector) 31 that has a thread groove 31a with which the threaded shaft 10 is engaged and that is fixed to the proximal end of the corresponding wire 6. The pulling mechanisms 7 are accommodated within an outer tube, serving as an outer sheath for the main portion 3, and are supported within a second part 320 (which will be described later) of the outer tube by a supporter 32 that supports the four motors 9.

Each motor 9 generates a rotational force that causes the corresponding shaft 8 to rotate about a central axis extending in the longitudinal direction thereof. When the shaft 8 rotates in the forward or reverse direction, the corresponding threaded shaft 10 rotates in the forward or reverse direction together with the shaft 8. Each movable members 31 has a columnar shape with a fan-shaped cross section, and the thread groove 31a thereof is formed in the curved outer peripheral surface that faces radially outward relative to the axis A. With forward or reverse rotation of the corresponding threaded shaft 10, the movable members 31 advances or retracts in the direction of the axis A relative to the main portion 3.

Referring to FIG. 3A, in an initial state, the movable members 31 are disposed at their initial positions so as to cause the bendable portion 5 to extend substantially straight along the axis A. When the movable members 31 advance or retract in the direction of the axis A from their initial positions, some of the four wires 6 are pushed out, whereas the remaining wires are pulled, causing the bendable portion 5 to bend as shown in FIG. 3B. By adjusting the amounts of pushing and pulling of the wires 6, the bending angle of the bendable portion 5 can be controlled.

Furthermore, the manipulator 1 includes a combination changing mechanism 33 that changes the combination of the wires 6, the movable members 31, and the pulling mechanisms 7 by rotating the pulling mechanisms 7 in units of substantially 45° around the axis A relative to the wires 6 and the movable members 31.

In detail, the outer tube of the main portion 3 has a first part 310 that is fixed to the proximal end of the bendable portion 5 and that partially accommodates the proximal ends of the wires 6, and the second part 320 that accommodates the pulling mechanisms 7. The combination changing mechanism 33 is formed of the second part 320 provided in a rotatable manner about the axis A relative to the first part 310, and a motor (not shown) that rotationally drives the second part 320.

When the second part 320 rotates, the pulling mechanisms 7 supported by the supporter 32 in the second part 320 rotate together with the second part 320. In this case, the threaded shafts 10 move along the outer peripheral surfaces of the four movable members 31 that constitute a cylindrical surface centered on the axis A, causing the threaded shafts 10 to newly engage with the thread grooves 31a of movable members 31 that are different from the movable members 31 previously engaged with the threaded shafts 10. Thus, the combination of the wires 6 and the pulling mechanisms 7 connected to the wires 6 is changed.

Figure 9:
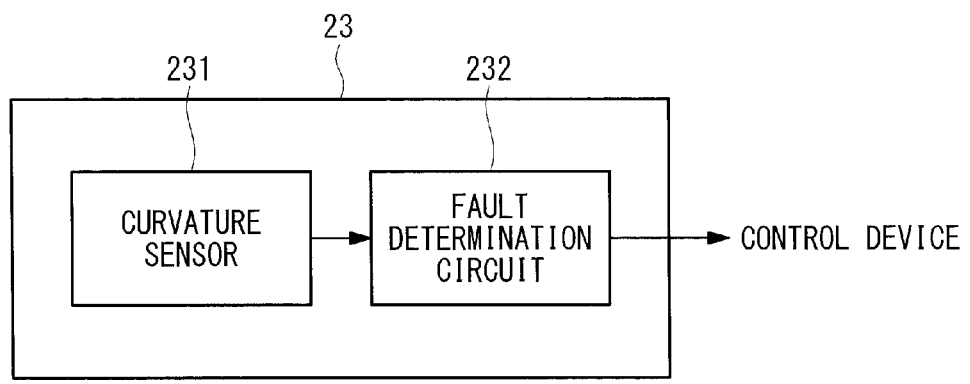
FIG. 9 is a block diagram illustrating the configuration of a fault detector.

Furthermore, referring to FIG. 9, the manipulator 1 includes the fault detector 23 that detects a fault in a pulling mechanism 7, as described in the first embodiment.

Next, the operation of the surgical manipulator system 100 equipped with the manipulator 1 having the above-described configuration will be described.

Figure 12:
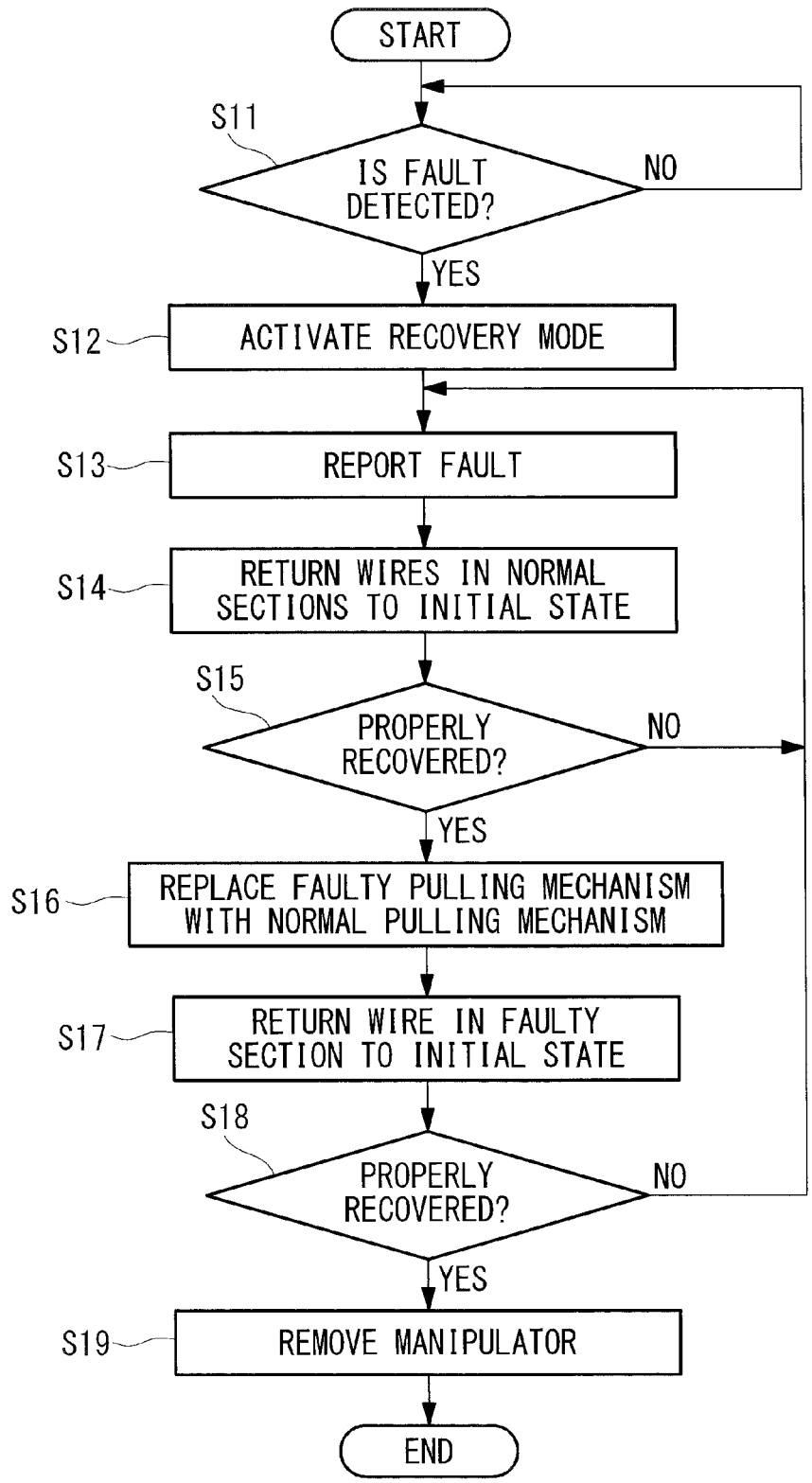
FIG. 12 is a flowchart explaining the operation of the surgical manipulator system when a pulling mechanism is faulty.

With the surgical manipulator system 100 according to this embodiment, if any of the pulling mechanisms 7 becomes faulty during the manipulation of the manipulator 1 such that the bendable portion 5 of the manipulator 1 does not move in response to an input manipulation performed on the input unit 81 by the surgeon Y, the fault detector 23 detects a fault in the pulling mechanism 7. Referring to FIG. 12, when a fault is detected (YES in step S11), the control device 60 activates a recovery mode (step S12) and executes a process for setting the bendable portion 5 in a state where it is removable from the body by using normal pulling mechanisms 7, as described below.

In the recovery mode, the control device 60 first notifies the surgeon Y of the fault in the same manner as the step S3 in the first embodiment (step S13).

Subsequently, the control device 60 drives the normal pulling mechanisms 7 in which a fault has not been detected, moves the movable members 31 to their initial positions, and returns the wires 6 to their initial states (step S14). In this case, the control device 60 checks whether or not the bending angle of the bendable portion 5 has properly changed in response to the driving of the pulling mechanisms 7 on the basis of the bending angle detected by the curvature sensor 231 of the fault detector 23 (step S15).

Figure 13A:
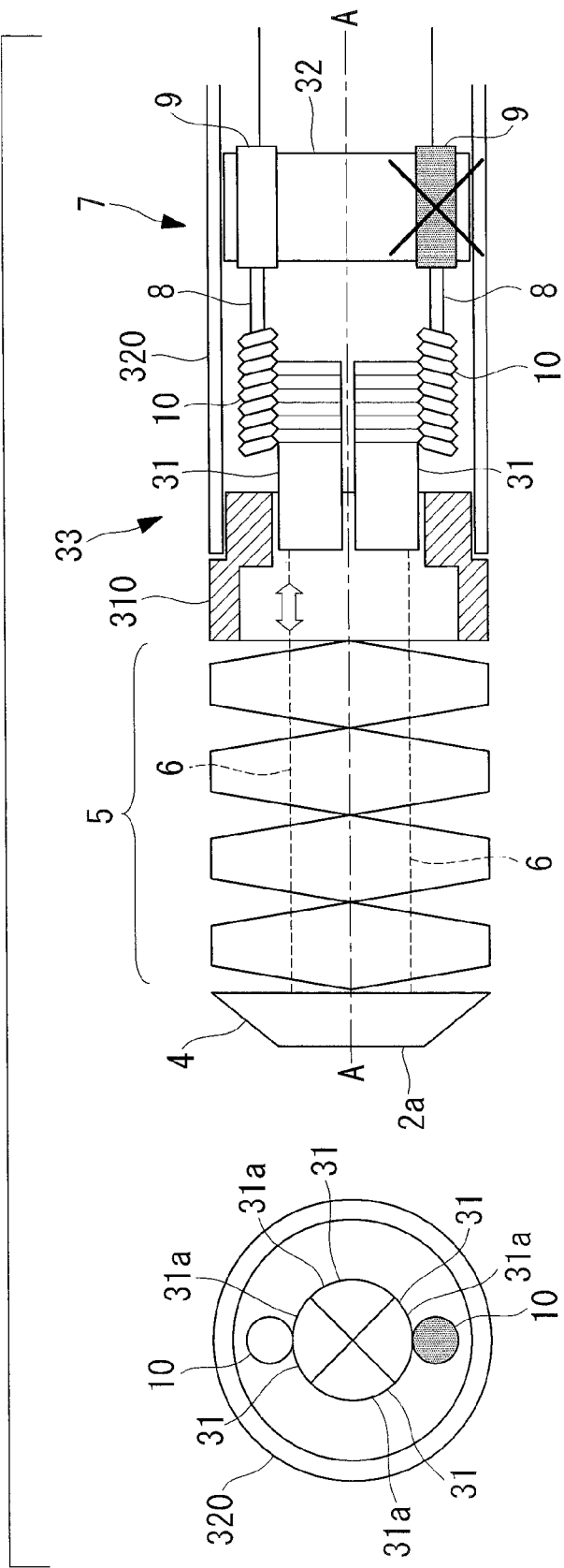
FIG. 13A illustrates how pulling mechanisms are moved by a combination changing mechanism.
Figure 13B:
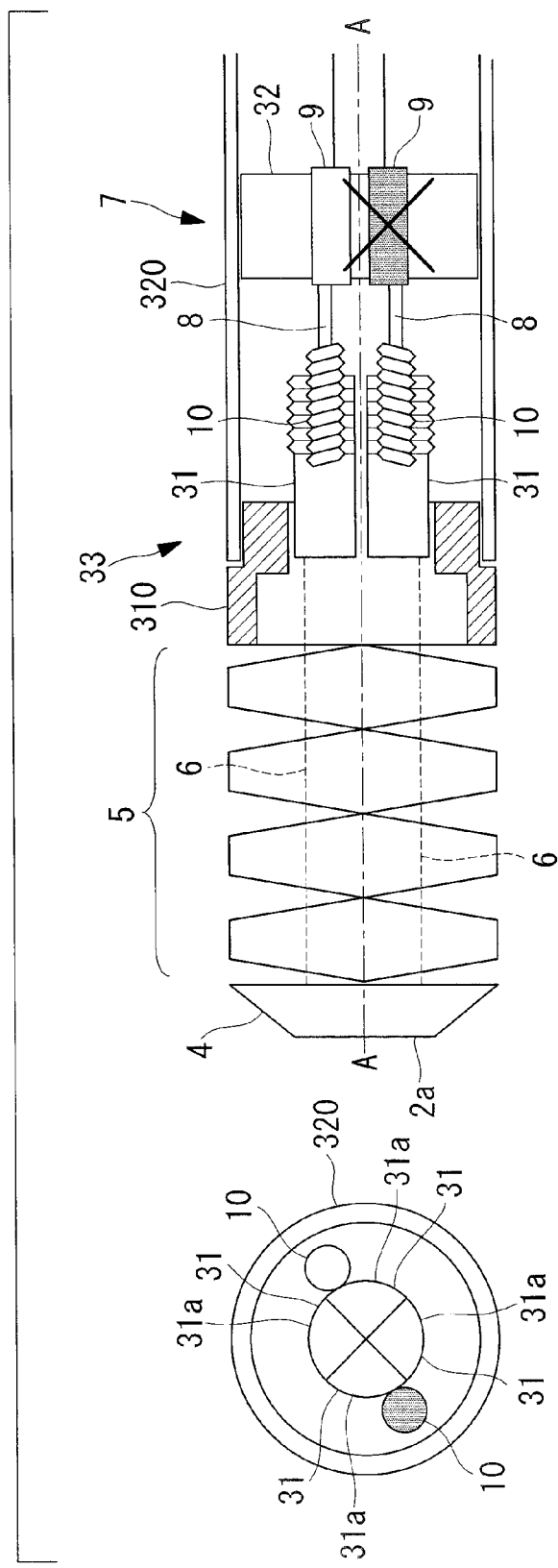
FIG. 13B illustrates how the pulling mechanisms are moved by the combination changing mechanism.
Figure 13C:
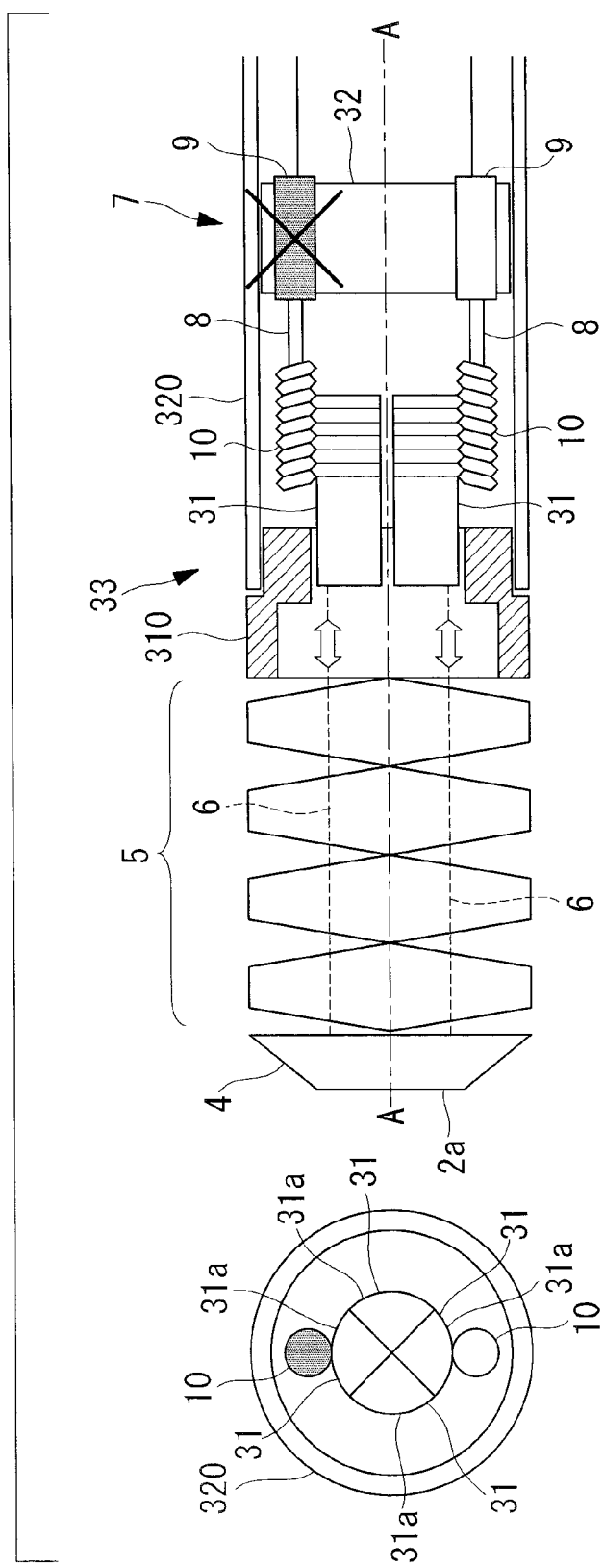
FIG. 13C illustrates how the pulling mechanisms are moved by the combination changing mechanism.

Then, referring to FIGS. 13A to 13C, the control device 60 actuates the combination changing mechanism 33 to rotate the second part 320 of the outer tube so that a normal pulling mechanism 7 is set at the position of the faulty pulling mechanism 7 (step S16). In FIGS. 13A to 13C, only two sets of wires 6 and pulling mechanisms 7 are illustrated to simplify the drawings. Subsequently, the wire 6 previously connected to the faulty pulling mechanism 7 is returned to its initial state by the normal pulling mechanism 7, as in steps S14 and S15 (steps S17 and S18). If faults in multiple pulling mechanisms 7 are detected, the process from step S16 to step S18 is repeated multiple times. Thus, all of the wires 6 are returned to their initial states, causing the bendable portion 5 to extend substantially straight along the axis A. In this state, the manipulator 1 is removed from the body (step S19).

When a pulling mechanism 7 is faulty in a state where the bendable portion 5 is bent, the corresponding wire 6 cannot be driven by using this pulling mechanism 7, thus leaving the bendable portion 5 in a rigidly bent state. With this embodiment, the faulty pulling mechanism 7 and a normal pulling mechanism 7 are switched by the combination changing mechanism 33 so that the wire 6 can be returned to its initial state by using the normal pulling mechanism 7, whereby the bendable portion 5 can be straightened out again. This is advantageous in that the manipulator 1 can be smoothly removed from the body.

In this embodiment, when a pulling mechanism 7 is faulty, the bending angle of the bendable portion 5 does not change properly in response to an input manipulation performed on the input unit 81 by the surgeon Y, and the field of view of the camera 25 displayed on the display unit 82 does not move properly. Therefore, the surgeon Y can readily recognize a fault in the pulling mechanism 7. In light of this, the surgeon Y may detect a fault in a pulling mechanism 7 and manually activate the recovery mode by, for example, pressing a switch (not shown).

In this embodiment, the threaded shafts 10 are disposed at the outer side of the movable members 31 in the radial direction. Alternatively, as shown in FIG. 14, the threaded shafts 10 may be disposed at the inner side of the movable members 31 in the radial direction.

The degree of bending of the bendable portion 5 caused by pushing and pulling of the wires 6 is dependent on the positions of the wires 6 in the radial direction. Specifically, the closer the connection position between the wires 6 and the distal end portion 4 is toward the outer side in the radial direction, the amounts of pushing and pulling of the wires 6 required for bending the bendable portion 5 by the same angle can be minimized. Therefore, by disposing the pulling mechanisms 7 at the inner side in the radial direction and disposing the movable members 31 and the wires 6 at the outer side in the radial direction, the bendable portion 5 can be bent more efficiently.

Figure 14:
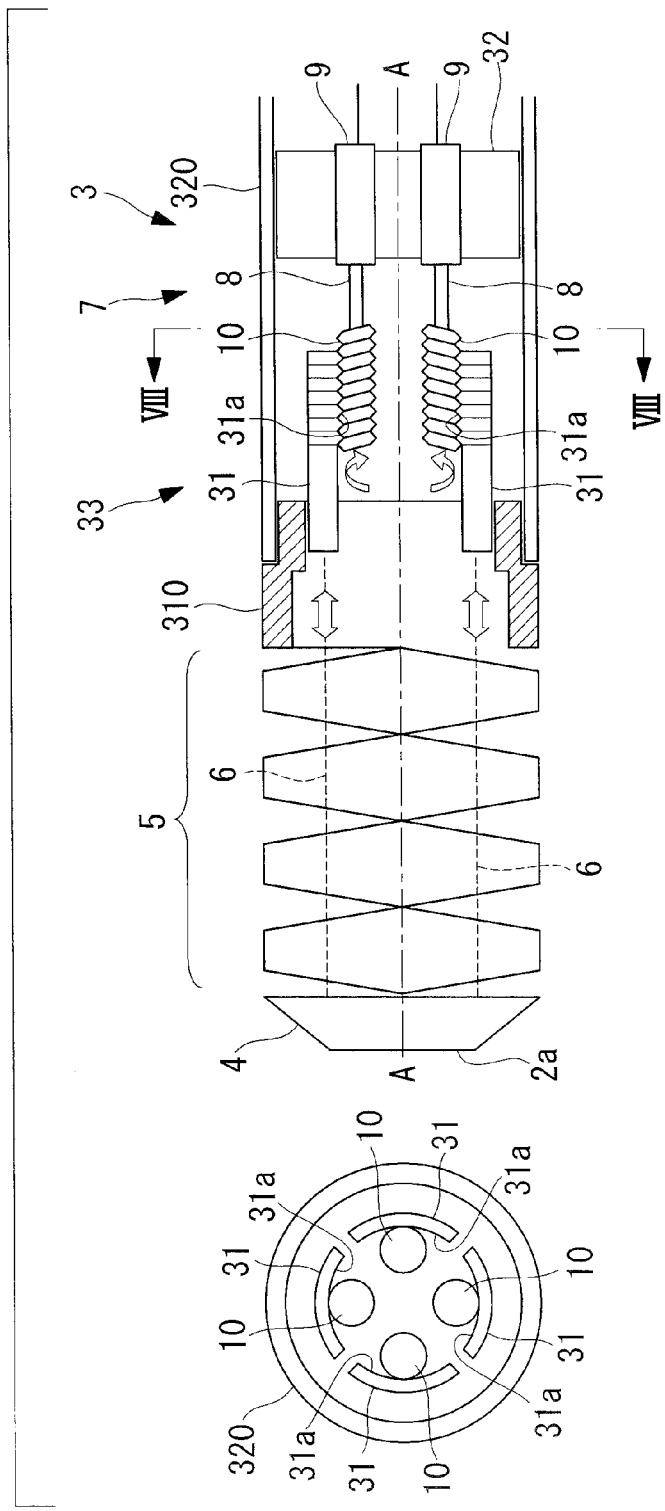
FIG. 14 includes a longitudinal sectional view (right side) illustrating a modification of the pulling mechanisms and a cross-sectional view (left side) taken along line VIII-VIII.

In this case, as shown in FIG. 14, each movable members 31 has a circular-arc cross-sectional shape centered on the axis A, and the thread groove 31a is formed in the inner peripheral surface thereof. With this configuration, when the pulling mechanisms 7 are rotated about the axis A by actuating the combination changing mechanism 33, the threaded shafts 10 can be readily moved along the inner peripheral surfaces in which the thread grooves 31a are formed.

In this embodiment, the combination changing mechanism 33 is described as being configured to rotate the pulling mechanisms 7 relative to the wires 6 and the movable members 31. However, the movement of the pulling mechanisms 7 when changing the combination is not limited thereto. For example, the combination of the wires 6, the movable members 31, and the pulling mechanisms 7 may be changed by linearly moving the pulling mechanisms 7.

Figure 15A:
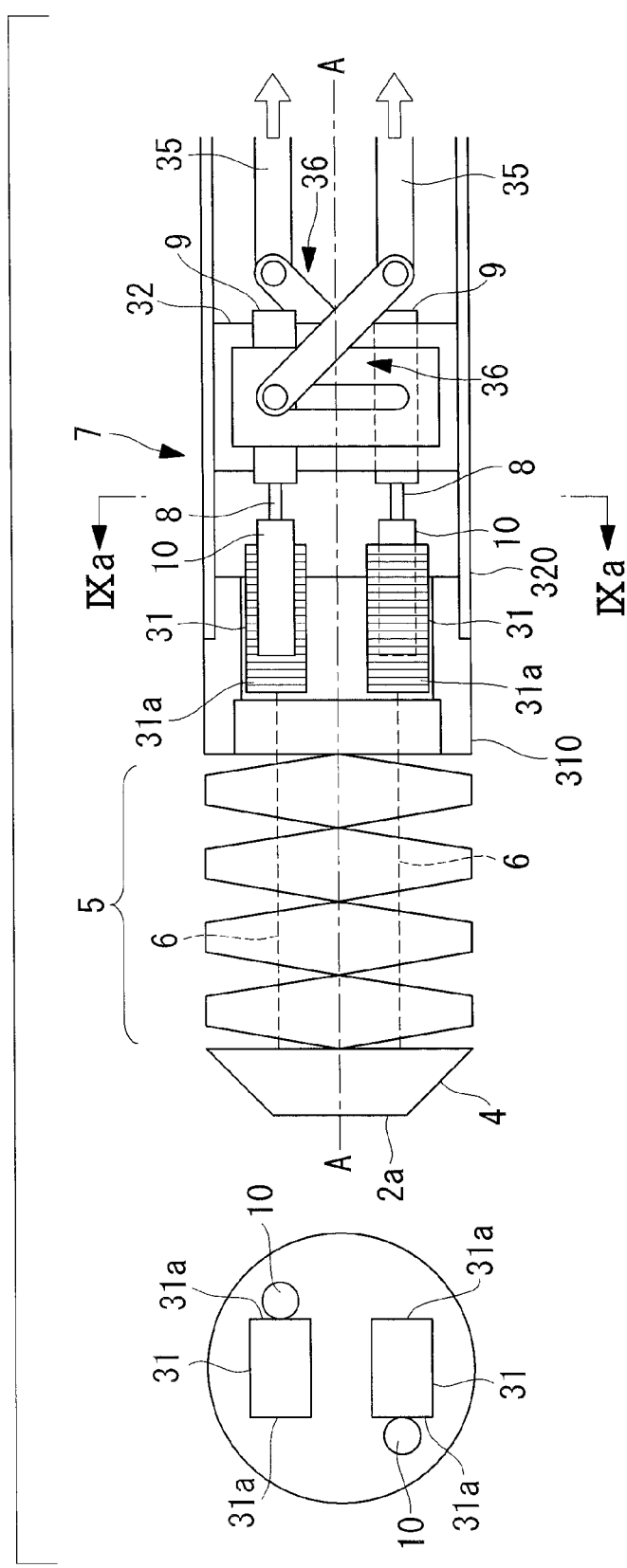
FIG. 15A illustrates the configuration of a modification of the combination changing mechanism, and includes a longitudinal sectional view (right side) illustrating how the pulling mechanisms are moved by the combination changing mechanism and a cross-sectional view (left side) taken along line IXa-IXa.
Figure 15B:
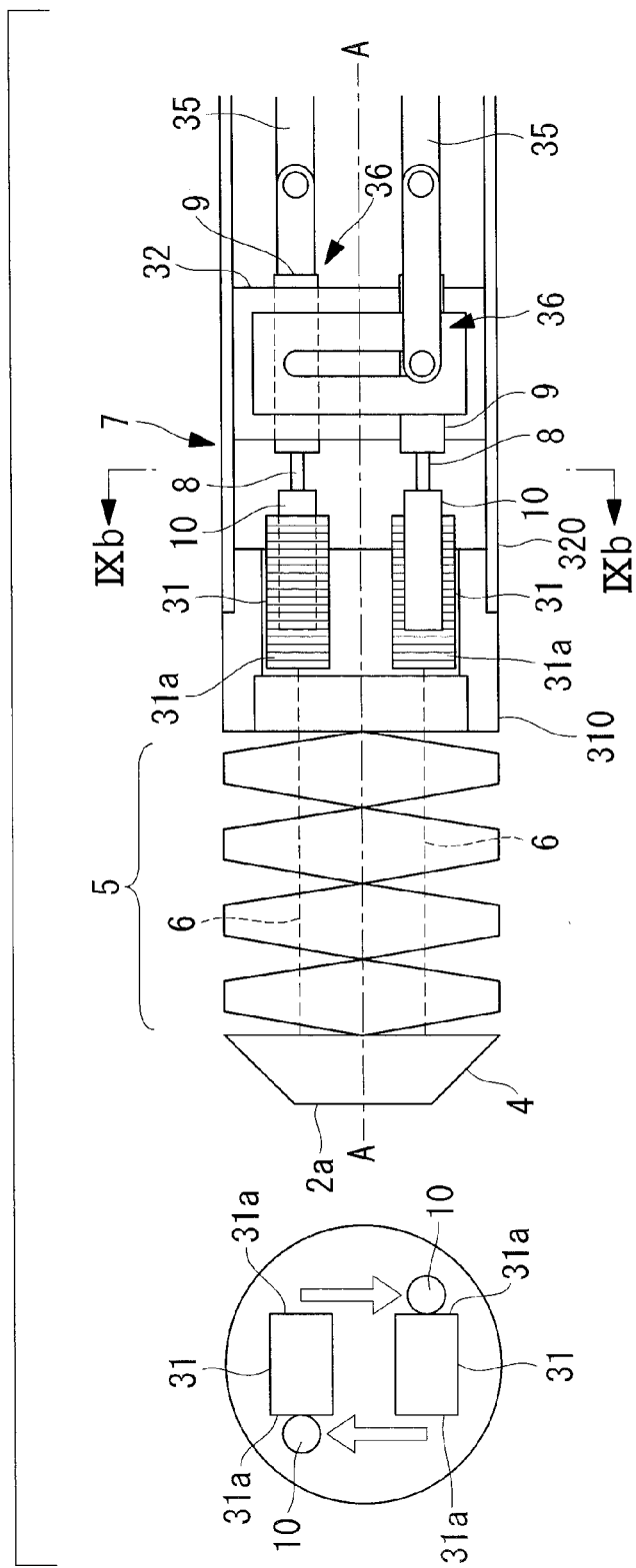
FIG. 15B illustrates the configuration of the modification of the combination changing mechanism, and includes a longitudinal sectional view (right side) illustrating how the pulling mechanisms are moved by the combination changing mechanism and a cross-sectional view (left side) taken along line IXb-IXb.

FIGS. 15A and 15B illustrate an example of the combination changing mechanism 33 that linearly moves the pulling mechanisms 7. In this configuration, two sets of wires 6, movable members 31, and pulling mechanisms 7 are provided at positions facing each other, with the axis A interposed therebetween. The pulling mechanisms 7 each include a lever 35 that is pushed and pulled in the direction of the axis A, and a link mechanism 36 that converts push-pull motion of the lever 35 into linear motion in a direction orthogonal to the axis A so as to move the pulling mechanism 7. In this configuration, the movable members 31 have thread grooves 31a in two surfaces that are engageable with the two threaded shafts 10.

Furthermore, although the drivers 9 are provided at the proximal end of the bendable portion in this embodiment, the positions of the drivers 9 are not limited thereto. For example, the drivers 9 may be provided at the proximal end of the manipulator 1.

Furthermore, although the manipulator 1 is described as being equipped with a camera 25 and a surgical tool 26 in the first and second embodiment, the camera 25 may be omitted where necessary.

In addition, the following aspects are lead from the individual embodiments described above.

A first aspect of the present invention is a manipulator including an elongated main portion, a distal end portion disposed at a distal end of the main portion, and a bendable portion provided between the main portion and the distal end portion; a plurality of linear members that are connected to the distal end portion and that extend to the main portion via the bendable portion; a power generator that generates power; a plurality of power transmitters that are provided in the main portion and that transmit, to proximal ends of the linear members, the power generated by the power generator as linear motion in a longitudinal direction of the main portion; and a linear-member relaxing unit that relaxes the plurality of linear members in which tension is generated between the distal end portion and the power transmitters by being pushing and pulling of the linear members in the longitudinal direction by the linear motion transmitted from the power transmitters.

According to the first aspect of the present invention, the power transmitters transmit, to the proximal ends of the linear members, the power generated by the power generator as linear motion. The linear members are pushed toward the distal end or pulled toward the proximal end. This causes the bendable portion disposed between the distal end portion and the connectors to bend.

In this case, if a power transmitter is faulty, the linear-member relaxing unit is actuated so as to relax the linear members in which tension is generated between the distal end portion and the power transmitters and that are maintaining the bent shape of the bendable portion, whereby the bendable portion is set in a deformable state in accordance with an external force. Consequently, even when the power generator or the power transmitters is/are faulty, smooth removal from the body is made possible, starting from the distal end portion inserted in the body to the main portion.

In the first aspect described above, the linear-member relaxing unit may cause the distal end portion and the plurality of power transmitters to relatively move in the longitudinal direction close to each other.

Accordingly, by actuating the linear-member relaxing unit, the distal end portion and the power transmitters are brought closer to each other so that the distance between the distal end portion and the power transmitters becomes shorter than the length of the linear members that connect the distal end portion and the power transmitters. Consequently, the plurality of linear members can be simultaneously relaxed.

In the first aspect described above, the linear-member relaxing unit may include a supporting member that simultaneously supports the plurality of power transmitters and that is movable together with the plurality of power transmitters in the longitudinal direction relative to the main portion, and a moving mechanism that moves the supporting member toward the distal end.

Accordingly, by actuating the moving mechanism, the supporting member moves toward the distal end so that the plurality of power transmitters move toward the distal end. Consequently, the plurality of power transmitters can be brought closer to the bendable portion.

In the first aspect described above, the linear-member relaxing unit may include a supporting member that supports a proximal end of the bendable portion, and a moving mechanism that moves the supporting member toward the proximal end.

Accordingly, by actuating the moving mechanism, the supporting member moves toward the proximal end so that the distal end portion moves toward the proximal end together with the bendable portion. Consequently, the distal end portion can be brought closer to the power transmitters.

In the first aspect described above, the moving mechanism may include a rotational-force generator that generates a rotational force, and a power converter that converts the rotational force generated by the rotational-force generator into linear motion in the longitudinal direction and transmits the linear motion to the supporting member.

Accordingly, with a simple configuration, the supporting member can be moved in the longitudinal direction of the main portion.

In the first aspect described above, the power transmitters may each include a shaft member that is disposed in the longitudinal direction in the main portion and that is rotated about an axis extending in the longitudinal direction by the power generated by the power generator, a threaded shaft member that connects the proximal end of the corresponding linear member to the shaft member and that is rotated together with the shaft member, and a nut member that is engaged with the threaded shaft member and that feeds the rotating threaded shaft member in the longitudinal direction.

Accordingly, the power of the power generator is converted from rotational motion of the shaft members into linear motion by the threaded shaft members and the nut members, and the linear motion is transmitted to the linear members. Consequently, the linear members can be pushed and pulled with a simple configuration.

A second aspect of the present invention is a manipulator including an elongated main portion, a distal end portion disposed at a distal end of the main portion, and a bendable portion provided between the main portion and the distal end portion; a plurality of linear members that are connected to the distal end portion and that extend to the main portion via the bendable portion; a plurality of pulling mechanisms provided in the main portion and having connectors that are connected to proximal ends of the linear members, drivers that generate rotational motion, and power converters that convert the rotational motion generated by the drivers into linear motion in a longitudinal direction and transmit the linear motion to the connectors; and a combination changing mechanism that changes a combination of the linear members and the pulling mechanisms connected to the linear members.

According to the second aspect of the present invention, the rotational motion generated by the drivers is converted into linear motion by the power converters, and the linear motion is transmitted to the connectors. The linear members connected to the connectors are pushed toward and pulled away from the distal end portion, causing the bendable portion disposed between the distal end portion and the connectors to bend.

In this case, if any of the plurality of pulling mechanisms is faulty, the combination changing mechanism is actuated so as to change the combination of linear members and pulling mechanisms. Consequently, even when the pulling mechanism is faulty in a state where the bendable portion is bent, the faulty pulling mechanism can be replaced with a normal pulling mechanism so that the bendable portion can be substantially straightened out again, whereby the insertion section can be smoothly removed from the body.

In the second aspect described above, the power converters may each include a shaft member that is disposed in a longitudinal direction of the main portion and that is rotated about a central axis thereof by the corresponding driver, a threaded shaft member that is coaxial with the shaft member and that is rotated together with the shaft member, and a movable member that has a thread groove engageable with the threaded shaft member and that is provided at the proximal end of the corresponding linear member in a movable manner in the longitudinal direction. Each connector may be formed of the threaded shaft member and the movable member.

Accordingly, since the linear members and the pulling mechanisms become connected due to the engagement between the threaded shaft members and the thread grooves of the movable members, the attachment and the detachment between the linear members and the pulling mechanisms can be readily performed when changing the combination thereof.

In the second aspect described above, the combination changing mechanism may change the combination of the linear members and the pulling mechanisms by moving the pulling mechanisms relative to the linear members.

Accordingly, of the linear members and the pulling mechanisms, since only a mechanism for moving the pulling mechanisms is required, the configuration can be simplified.

In the second aspect described above, the main portion may include a tubular outer tube having a first part that is fixed to the bendable portion and a second part that is provided at a proximal end of the first part in a rotatable manner in a circumferential direction relative to the first part and that accommodates the pulling mechanisms. The combination changing mechanism may move the pulling mechanisms relative to the linear members by rotating the pulling mechanisms together with the second part.

Accordingly, the pulling mechanisms can be moved with further simplified operation.

In the second aspect described above, a fault detector that detects a fault in the pulling mechanisms may be further provided. The combination changing mechanism may change the combination of the linear members and the pulling mechanisms when the fault detector detects a fault in the pulling mechanisms.

Accordingly, the detection of a fault in a pulling mechanism and the changing of the combination of linear members and pulling mechanisms by the combination changing mechanism can be performed automatically.

REFERENCE SIGNS LIST 1 manipulator
2 insertion section
3 main portion
310 outer tube, first part
320 outer tube, second part
4 distal end portion
5 bendable portion
5a joint ring
6 wire (linear member)
7 pulling mechanism
8 shaft (shaft member, power transmitter, power converter)
9 motor (power generator)
10 threaded shaft (threaded shaft member, power transmitter, connector, power converter)
11 nut (nut member, power transmitter, supporting member)
12 wire relaxing unit (linear-member relaxing unit)
13 moving mechanism
14 shaft (power converter)
15 motor (rotational-force generator)
16 threaded shaft (power converter)
17 nut (power converter)
18 positioning member
19 positioning releasing mechanism
20 manipulable section
21 shaft
22 stopper
23 fault detector
231 curvature sensor
232 fault determination circuit
24 light unit
25 camera
26 surgical tool
26a joint
31 movable member (connector)
31a thread groove
32 supporter
33 combination changing mechanism
35 lever
36 link mechanism
40 bed
60 control device
80 manipulation device
81 input unit
82 display unit
100 surgical manipulator system
X patient
Y surgeon

The invention claimed is:

1. A manipulator comprising:
an elongated main portion, a distal end portion disposed at a distal end of the main portion, and a bendable portion provided between the main portion and the distal end portion;
a plurality of linear members that are connected to the distal end portion and that extend to the main portion via the bendable portion;
a power generator that generates power;
a plurality of power transmitters that are provided in the main portion and that transmit, to proximal ends of the linear members, the power generated by the power generator as linear motion in a longitudinal direction of the main portion; and
a linear-member relaxing unit that relaxes the plurality of linear members in which tension is generated between the distal end portion and the power transmitters by pushing and pulling of the linear members in the longitudinal direction by the linear motion transmitted from the power transmitters;
wherein the power transmitters each include
a shaft member that is disposed in the longitudinal direction in the main portion and that is rotated about an axis extending in the longitudinal direction by the power generated by the power generator,
a threaded shaft member that connects the proximal end of the corresponding linear member to the shaft member and that is rotated together with the shaft member, and
a nut member that is engaged with the threaded shaft member and that feeds the rotating threaded shaft member in the longitudinal direction.

2. The manipulator according to claim 1, wherein the linear-member relaxing unit causes the distal end portion and the plurality of power transmitters to relatively move in the longitudinal direction close to each other.

3. The manipulator according to claim 2, wherein the linear-member relaxing unit includes a supporting member that simultaneously supports the plurality of power transmitters and that is movable together with the plurality of power transmitters in the longitudinal direction relative to the main portion, and a moving mechanism that moves the supporting member toward the distal end.

4. The manipulator according to claim 2, wherein the linear-member relaxing unit includes a supporting member that supports a proximal end of the bendable portion, and a moving mechanism that moves the supporting member toward the proximal end.

5. The manipulator according to claim 3,
wherein the moving mechanism includes
a rotational-force generator that generates a rotational force, and
a power converter that converts the rotational force generated by the rotational-force generator into linear motion in the longitudinal direction and transmits the linear motion to the supporting member.

6. The manipulator according to claim 4,
wherein the moving mechanism includes
a rotational-force generator that generates a rotational force, and
a power converter that converts the rotational force generated by the rotational-force generator into linear motion in the longitudinal direction and transmits the linear motion to the supporting member.

7. A manipulator comprising:

an elongated main portion, a distal end portion disposed at a distal end of the main portion, and a bendable portion provided between the main portion and the distal end portion;

a plurality of linear members that are connected to the distal end portion and that extend to the main portion via the bendable portion;

a plurality of pulling mechanisms provided in the main portion and having connectors that are connected to proximal ends of the linear members, drivers that generate rotational motion, and power converters that convert the rotational motion generated by the drivers into linear motion in a longitudinal direction and transmit the linear motion to the connectors; and a combination changing mechanism that changes a combination of the linear members and the pulling mechanisms connected to the linear members;

wherein the power converters each include a shaft member that is disposed in a longitudinal direction of the main portion and that is rotated about a central axis thereof by the corresponding driver, a threaded shaft member that is coaxial with the shaft member and that is rotated together with the shaft member, and a movable member that has a thread groove engageable with the threaded shaft member and that is provided at the proximal end of the corresponding linear member in a movable manner in the longitudinal direction, and wherein each connector is formed of the threaded shaft member and the movable member.

8. The manipulator according to claim 7, wherein the combination changing mechanism changes the combination of the linear members and the pulling mechanisms by moving the pulling mechanisms relative to the linear members.

9. The manipulator according to claim 8, wherein the main portion includes a tubular outer tube having a first part that is fixed to the bendable portion and a second part that is provided at a proximal end of the first part in a rotatable manner in a circumferential direction relative to the first part and that accommodates the pulling mechanisms, and wherein the combination changing mechanism moves the pulling mechanisms relative to the linear members by rotating the pulling mechanisms together with the second part.

10. The manipulator according to claim 7, further comprising:

a fault detector that detects a fault in the pulling mechanisms, wherein the combination changing mechanism changes the combination of the linear members and the pulling mechanisms when the fault detector detects a fault in the pulling mechanisms.

* * * * *